United States Patent

Yokoyama et al.

(10) Patent No.: US 6,522,149 B2
(45) Date of Patent: Feb. 18, 2003

(54) METHOD AND APPARATUS FOR IDENTIFYING PLASTICS

(75) Inventors: Sadahiko Yokoyama, Tokyo (JP); Takaaki Matsushima, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/843,890

(22) Filed: Apr. 30, 2001

(65) Prior Publication Data

US 2001/0054900 A1 Dec. 27, 2001

(30) Foreign Application Priority Data

May 15, 2000 (JP) ........................................ 2000-142360
Nov. 2, 2000 (JP) ........................................ 2000-336032

(51) Int. Cl.[7] ............................................. G01N 27/60
(52) U.S. Cl. ...................... 324/453; 209/11; 209/127.1
(58) Field of Search ................................. 324/452, 453, 324/454, 513, 515, 458, 457, 520, 519, 517, 548, 551; 209/576, 577, 587, 127.1, 509, 522, 11, 127.2

(56) References Cited

U.S. PATENT DOCUMENTS

| | | | | |
|---|---|---|---|---|
| 5,134,291 A | * | 7/1992 | Ruhl et al. ................... 250/341 |
| 5,141,110 A | * | 8/1992 | Trishan et al. ............... 209/524 |
| 5,318,172 A | * | 6/1994 | Kenny et al. ................ 209/524 |
| 5,397,066 A | * | 3/1995 | Leitman et al. ................ 241/19 |
| 5,510,619 A | * | 4/1996 | Zachmann et al. ..... 250/339.08 |
| 5,608,326 A | * | 3/1997 | Mucci et al. ................ 324/454 |
| 5,615,778 A | * | 4/1997 | Kaiser et al. ................ 209/578 |
| 5,794,788 A | * | 8/1998 | Massen ........................ 209/524 |
| 6,084,149 A | * | 7/2000 | Akae et al. .................. 588/237 |
| 6,271,492 B1 | * | 8/2001 | Machata et al. .......... 209/127.1 |

FOREIGN PATENT DOCUMENTS

| | | |
|---|---|---|
| JP | 5-196587 | 8/1993 |
| JP | 6-63945 | 3/1994 |
| JP | 6-229957 | 8/1994 |
| JP | 7-111397 | 11/1995 |
| JP | 8-300354 | 11/1996 |
| JP | 8-309749 | 11/1996 |
| JP | 9-269286 | 10/1997 |
| JP | 9-297114 | 11/1997 |
| JP | 9-299829 | 11/1997 |
| JP | 11-323005 | 11/1999 |

OTHER PUBLICATIONS

K. Murata, "System for producing powder fuels from refuse plastics", Chemical Device, Feb. 1995, pp. 33–35.

\* cited by examiner

Primary Examiner—Christine Oda
Assistant Examiner—Etienne LeRoux
(74) Attorney, Agent, or Firm—Sughrue Mion, PLLC

(57) ABSTRACT

Waste plastics, which contain coloring agents and are in various forms, are heated and electrified to divide into three groups in order to collect them without crushing while maintaining their product forms. Each group consists of high exothermic plastics, low exothermic plastics or PVC.

33 Claims, 7 Drawing Sheets

METHOD AND APPARATUS FOR IDENTIFYING PLASTICS

BACKGROUND OF THE INVENTION

1. Field of the Invention

The present invention relates to a method and an apparatus for identifying plastics of unknown materials.

2. Description of the Related Art

To identify materials of unknown objects in the art, JP 7-111397(B2) and JP 8-300354(A) publications describe methods of applying infrared rays on objects to identify them on the basis of differences, for example, in absorption spectrum, and amount of transmitted and reflected infrared rays.

To classify waste plastics into their types, JP 7-124053 application describes a method and apparatus for classifying plastics, which heats plastic fragments with microwaves and using a temperature difference between plastics. This classifying apparatus comprises: a crushing device for crushing waste plastics into a given size; a heating furnace for preheating crushed plastic fragments; a microwave oven for heating the preheated plastic fragments with microwaves; a radiation thermometer for measuring temperatures of the plastic fragments; and a classifying section for classifying the plastics on the basis of the results of measured temperatures. In the microwave heating, heat efficiency depends on permittivity. Therefore, the apparatus measures temperatures of plastic fragments after microwave heating and uses airflow to blow away only such plastic fragments for classification that are heated up to a temperature within a given range. In this apparatus, the heating furnace for preheating is used to enlarge differences in temperatures of plastics.

JP 8-113391 application describes a method and an apparatus for classifying plastics, which heats plastics with infrared rays and uses the temperature difference between plastics. This method and apparatus demonstrates examples identified through the use of temperature differences resulting from amounts of infrared rays absorbed by polyethylene terephthalate (hereinafter referred to as "PET") and polyvinyl chloride (hereinafter referred to as "PVC").

JP8-122868 application describes a method and an apparatus for classifying plastics, which frictionally electrifies plastic fragments in an electrifying container and uses differences in polarity and charged amount between the plastic fragments. When plastics of different types are frictionally contacted with each other, their electrostatic properties and charged amounts tend to differ in accordance with materials. In this apparatus, the plastic fragments are frictionally contacted with a frictional medium in the electrifying container. Then, the charged plastic fragments are supplied through electrodes that have a high potential therebetween to classify them for collection into one that adheres on one electrode, one that does not adhere on electrodes, and one that is attracted to the other electrode. A classifying apparatus using this method includes an electrostatic plastic separation device available from Hitachi Zosen Inc.

The conventional method, which uses differences in absorption, transmission and reflection properties for infrared rays, has a disadvantage because it fundamentally uses a ray of light and can not identify materials of colored objects. In particular, in wastes, objects are hardly identified because they are in various forms and mixed.

The method, which uses temperature differences resulting from heating with microwaves, has an extremely high possibility to generate discharges (sparks) when a metal is mixed in objects to be heated and a risk to fire plastics. In addition, JP 7-124053 preheats plastics at 80° C. for increasing an identification rate but temperatures of the plastics finally elevate near to or over 100° C. occasionally. In such a case, there is a risk to melt or decompose the plastics partly, which gives a large disadvantage for safety. Furthermore, even if identifying of plastics succeeds, it is difficult to blow plastic fragments in order to efficiently identify because they do not have a constant weight. Accordingly, this method is not possible to identify the plastic products that are not crashed. Further, the microwave oven has a large size and requires microwave shields in consideration of influences on human beings. As obvious from the forgoing, the apparatus, which uses microwave heating, is hardly applicable to a waste processing system that requires a high identification rate, a low cost and high safety.

The method and apparatus for identifying plastics, which heats plastics with infrared rays and uses the temperature difference between plastics, cannot identify PVC from other plastics. In consideration of a period of time from heating to measurement, a measured error and stability of the heating device, about 5 degrees of Centigrade is an enough temperature difference to identify temperatures by this method. Polymethyl methacrylate (Methacrylic resin; hereinafter referred to as "PMMA") and polystyrene (hereinafter referred to as "PS"), however, cannot be identified from PVC. The apparatus described in JP 8-113391 demonstrates examples identifying PVC bottles from PET bottles. Its identification rate is extremely lowered when plastics of other types than the above and plastics of other forms than bottles are mixed.

The method and apparatus for classifying plastics, which frictionally electrifies plastic fragments in the electrifying container and uses differences in polarity and charged amount between the plastic fragments, is difficult to perform identification efficiently. For example, in identifying a mixture of PVC fragments and polyethylene (hereinafter referred to as "PE") fragments, when PVC fragments contact PE fragments in the electrifying container, PE fragments tend to be charged positively and PVC fragments, negatively. When PE fragments contact with each other or when PVC fragments contact with each other, electrostatic polarity and charged amounts greatly vary in accordance with frictional situations. Even if PE fragments are charged positively and PVC fragments, negatively, when weights and sizes of plastic fragments are different, electrostatic force and gravity imparted on plastic fragments may differ. Therefore, the method of identifying, depending on electrostatic force as described in JP 8-122868, is difficult to perform identification efficiently. Thus, a crushing step is essentially required to equate sizes of plastics. It is extremely difficult, however, to crush all waste plastics in various forms into a given particle diameter and greatly increases the cost. Furthermore, an increased number of plastic fragment types make it more difficult to control charged amounts and impossible to identify general waste plastics.

On the other hand, in appropriately processing and recycling wastes, there is a high possibility to generate toxic substances on burning and heating the wastes if PVC is mixed therein, and a technique is needed to identify and remove PVC from the wastes. It is very difficult, however, for the conventional method to identify and remove only PVC. If the wastes with PVC mixed therein are burned easily, toxic substances, represented by dioxin, are possibly generated due to chlorine derived from PVC. A proposed method can make toxic substances harmless just when they are generated, but it requires an extremely expensive chemical facility and is not practical.

In reusing collected plastics as a refuse derived fuel (hereinafter referred to as "RDF") or a raw material for a blast furnace, it is very important to increase qualities of the collected plastics. For example, an RDF is required to have a high calorific value and a constant amount of heat. If a high exothermic plastic and a low exothermic plastic are mixed, such an RDF cannot be obtained. In particular, for a power generation system that uses an RDF, a high-quality RDF is requested. Currently, the high-quality RDF is not developed progressively, and there is a disadvantage in that an efficiency of power generation is extremely low. In the raw material for the blast furnace, it is required to mix high exothermic plastics and low exothermic plastics in a constant mixing amount in order to run the blast furnace in stably. Furthermore, if PVC is mixed in an RDF or in the raw material for the blast furnace, there is a high possibility to generate a toxic gas and a corrosive gas such as chlorine due to burning. These gases impart a great deal of influence on human beings and the blast furnace system, and adequate countermeasures are required.

If the wastes are crashed into small fragments, desired materials are hardly identified and collected efficiently from the crushed fragments. In consideration of crashing processes, dust countermeasures, noise countermeasures, treatments of collected materials and costs for transportation and so forth, it is preferred to construct a system that can identify the collected products as such on material basis, collect and supply them to the following process step.

SUMMARY OF THE INVENTION

Accordingly, a subject of the present invention is to provide a method and an apparatus for identifying waste plastics efficiently. More particularly, it is to provide a method and an apparatus for identifying waste plastics, which contain coloring agents and are in various forms, into three groups consisting of high exothermic plastics, low exothermic plastics and PVC, and for collecting them without crushing while maintaining their product forms.

Accordingly, the present invention is embodied as follows:

A first aspect of the present invention is a method of identifying plastics comprising: heating and electrifying a mixture of at least two plastics; and measuring heating properties and electrostatic properties thereof to identify the plastics.

A second aspect of the present invention is a method of identifying plastics comprising: heating, followed by electrifying, a mixture of at least two plastics; and measuring heating properties and electrostatic properties thereof to identify the plastics.

A third aspect of the present invention is a method of identifying plastics comprising: electrifying, followed by heating, a mixture of at least two plastics; and measuring electrostatic properties and heating properties thereof to identify the plastics.

A fourth aspect of the present invention is a method of identifying plastics comprising: simultaneously heating and electrifying a mixture of at least two plastics; and measuring heating properties and electrostatic properties thereof to identify the plastics.

Suitable conditions are described hereunder to carry out any one of the above-mentioned four aspects of the present invention.

The mixture includes at least one low exothermic plastic, at least one high exothermic plastic, and polyvinyl chloride.

The mixture is heated to identify the high exothermic plastic on the basis of a difference in heating property, followed by electrifying a mixture of the low exothermic plastic and the polyvinyl chloride to identify the polyvinyl chloride on the basis of a difference in electrostatic property.

The mixture is electrified to identify the low exothermic plastic on the basis of a difference in electrostatic property, followed by heating a mixture of the high exothermic plastic and the polyvinyl chloride to identify the polyvinyl chloride on the basis of a difference in heating property.

The heating comprises radiation of far infrared rays.

The electrifying comprises any one of corona discharge, frictional electrification, and a combination of corona discharge and frictional electrification.

The low exothermic plastic has, as essential components, polystyrene, polyethylene terephthalate, acrylonitrile-butadiene-styrene copolymer and methacrylic resin.

The high exothermic plastic has, as essential components, polyethylene and polypropylene.

The mixture comprises plastic products or wastes of plastic products.

The mixture is not crashed.

A fifth aspect of the present invention is an apparatus for identifying plastics comprising: a heating device for heating the plastics; an electrifying device for electrifying the plastics; a temperature-measuring device for measuring temperatures of the plastics; an electrification-measuring device for measuring charged states of the plastics; a display for displaying measured results of the temperatures; and a display for displaying measured results of the charged states, wherein the apparatus is operable in accordance with the method of identifying plastics as recited in any one of the above-mentioned four aspects of the present invention.

Suitable conditions are described hereunder to carry out the above-mentioned fifth aspect of the present invention.

The heating device comprises a device that uses far infrared rays, and a device that comprises a far infrared heater and a concave reflector, the reflector collecting far infrared rays to apply them on an object to be heated.

The electrifying device comprises a device that is operable in a way according to any one of corona discharge, frictional electrification, and a combination of corona discharge and frictional electrification, a device that comprises a plurality of stylus-like protrusions; corona discharge electrodes configured with fixed portions of the protrusions; and a power supply for applying a DC or AC voltage on the corona discharge electrodes, and a device that comprises a frictional medium; a fixing section for fixing the frictional medium; and a containing section for containing the frictional medium.

The frictional medium is one selected from the group consisting of a roller, a blush and a rod.

The electrifying device comprises a roller-like frictional medium and an auxiliary roller opposite thereto, the electrifying device interposing the plastics between the frictional medium and the auxiliary roller to frictionally electrifying the plastics.

The frictional medium has a portion composed of polyvinyl chloride for coming into contact with the plastics.

The polyvinyl chloride comprises soft polyvinyl chloride alone or a mixture of soft polyvinyl chloride and a plasticizer of 25–50% by weight of the mixture.

The temperature-measuring device comprises a device for outputting the measured results of temperatures to the display as temperature image data.

The electrification-measuring device comprises a device for measuring surface charges, surface potentials, or surface charges together with surface potentials on the plastics and outputting them to the display as charged data.

The display comprises a device for image-projecting the temperature image data input as such on the object measured by the temperature-measuring device, a device for image-projecting the charged data input as such on the object measured by the electrification-measuring device, or a marking means for adding identified marks on the plastics, the mark being classified on the basis of measured data input.

Other features and advantages of the invention will be apparent from the following description of the preferred embodiments thereof.

BRIEF DESCRIPTION OF THE DRAWINGS

The present invention will be more fully understood from the following detailed description with reference to the accompanying drawings in which.

DETAILED DESCRIPTION OF THE PREFERRED EMBODIMENTS

Methods and apparatuses for identifying plastics of the present invention will now be described in detail with reference to FIGS. 1–4.

Figure 1:
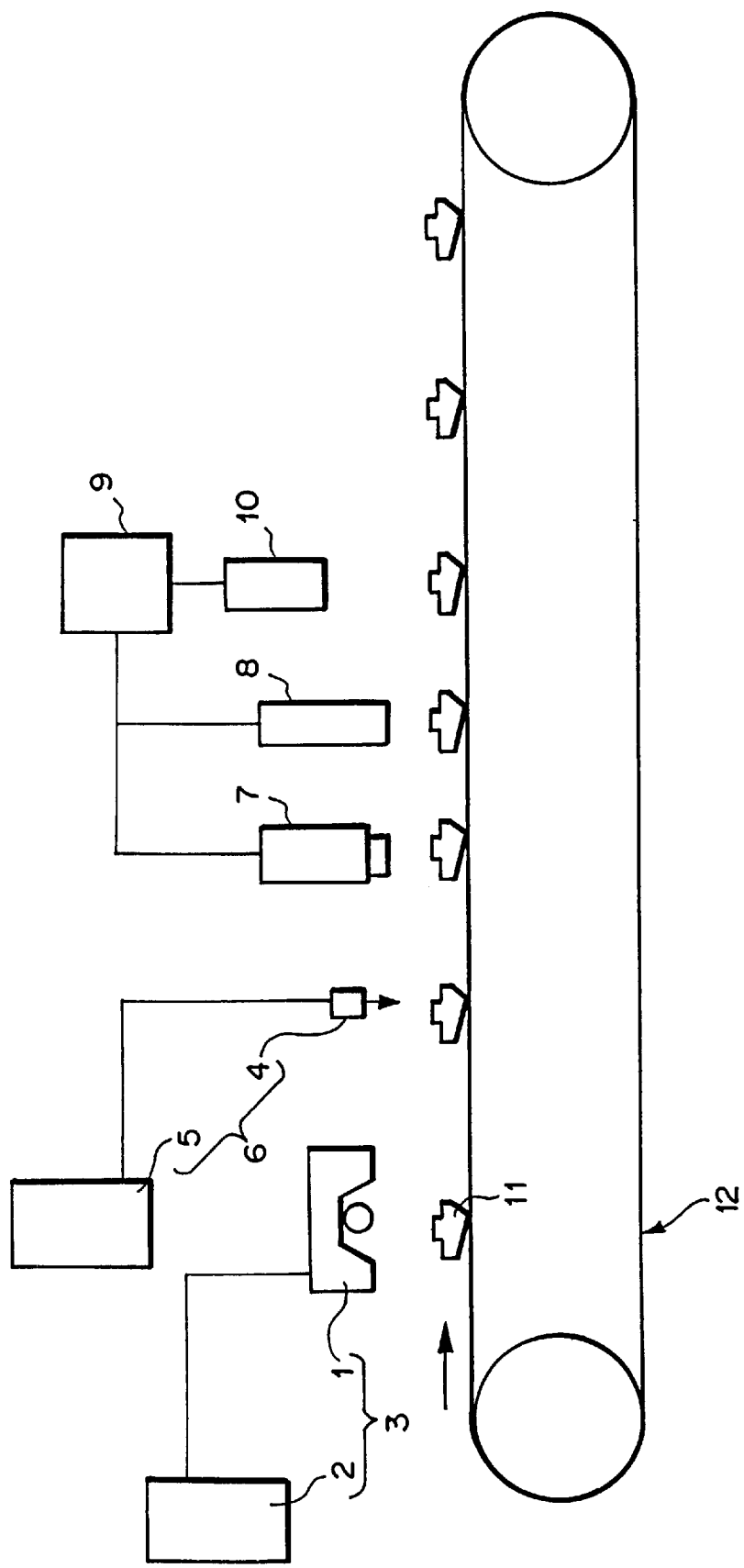
FIG. 1 is a schematic diagram showing an example of an apparatus for identifying plastics according to the present invention.

FIG. 1 is a schematic diagram showing an example of the apparatus for identifying plastics according to the present invention.

In accordance with the present invention, the apparatus for identifying plastics comprises a conveying device 12, a heating device 3, an electrifying device 6, a temperature-measuring device 7, an electrification-measuring device 8 and a display 10. A separation device may be used, if needed, which is operable in association with the display 10 and the conveying device 12.

In FIG. 1, plastics 11 of unknown materials are heated by the heating device 3 and are electrified by the electrifying device 6. The temperature-measuring device 7 measures their temperatures after heating and the electrification-measuring device 8 measures their surface potentials. Plastics 11 that satisfy a preset temperature, electrostatic polarity and/or charged amount are determined as objective plastics to be identified, and the display 10 indicates determined results.

Specific examples will be described below while the method and apparatus for identifying plastics according to the present invention are not limited to them.

EXAMPLE 1

A first example is described with reference to FIG. 1. In Example 1, above the conveying device 12, along the direction in which the plastics 11 of unknown materials are supplied, the heating device 3, the electrifying device 6, the temperature-measuring device 7, the electrification-measuring device 8 and the display 10 are arranged in order.

The conveying device 12 has a metallic belt conveyer of which belt portion is grounded. The heating device 3 can apply constant far infrared rays on the plastics 11 from a far infrared heater 1 that is located above the conveying device 12 and controlled by a temperature controller 2. A corona electrode 4 is configured to have stainless styluses that arrayed at an equal interval on a stainless rectangular rod along the length thereof. When a high DC voltage of about 20 kV is applied from a power supply 5 on the corona electrode 4, ions are generated by the corona discharge phenomenon at the proximity of stylus tips of the corona electrode 4. The electrifying device 6 uses the ions to electrify the plastics 11. The temperature-measuring device 7 uses an infrared thermograph that can perform a non-contact measurement of surface temperatures of the plastics 11 to measure a two-dimensional distribution of temperatures. In the electrification-measuring device 8, a plurality of surface potential sensors is arranged above the conveying device 2 to measure a two-dimensional distribution of surface potentials. The surface potential sensors use an electrostatic induction phenomenon, in which electric charges are generated on a metal that closes to the surface charges on the object, and monitor amounts of charges generated on small metallic plates to measure surface potentials on the objects. The two-dimensional measured results are input to the display 10 from the temperature-measuring device 7 and the electrification-measuring device 8 through a controller 9. The display 10 determines to identify it as an identified object if the object satisfies a preset temperature and surface potential. The display 10 comprises a marking device (not shown) to attach an ID mark on the identified object by painting.

For example, PE, PMMA and PVC are mixed in a mixture of plastics. This case is described below. These plastics are in the form of products such as bags and bottles. PE has components consisting only of carbon and hydrogen atoms and a calorific value of 10,300 kcal/kg equal to or more than that of the petroleum. On the other hand, PMMA contains oxygen atoms as components and accordingly has a calorific value of 5,000–6,000 kcal/kg less than that of the petroleum.

Temperatures of respective plastics after heating 30 seconds by the infrared heater are given in Table 1. Temperatures of PE, PMMA and PVC are 34.7° C., 40.8° C. and 43.4° C., respectively.

TABLE 1

| Materials | Temperatures (° C.) 30 seconds after far infrared heating |
|---|---|
| PE | 34.7 |
| PP | 35.6 |
| PS | 45.0 |
| PET | 59.2 |
| PMMA | 40.8 |
| ABS | 43.5 |
| PVC | 43.3 |

Figure 2:
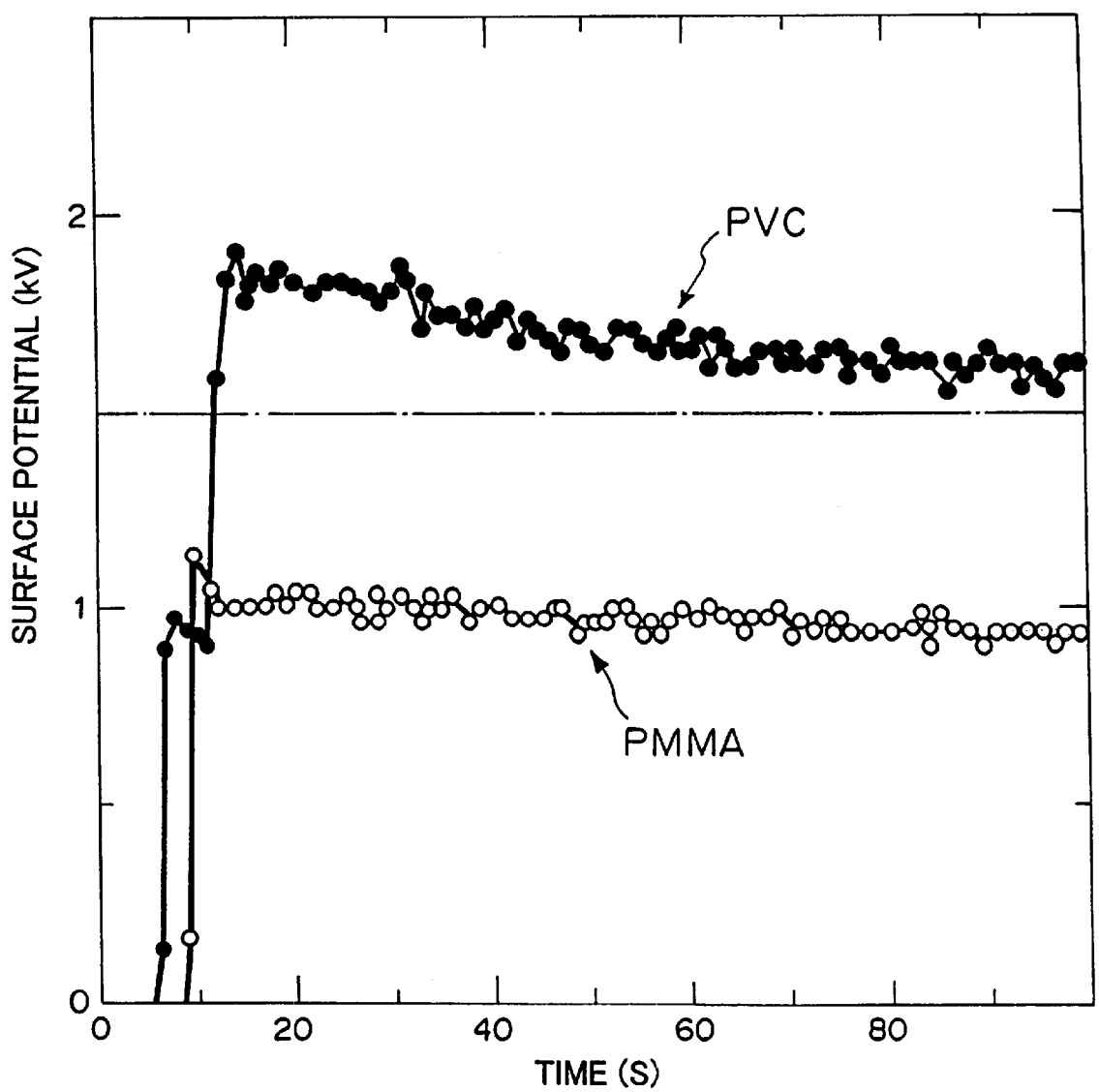
FIG. 2 shows a relation between surface potentials on corona-electrified plastics and a period of time.

FIG. 2 shows time variations of surface potentials on PMMA and PVC charged when a DC voltage of 20 kV is applied on the corona electrode.

A positional relation between the temperature- and electrification-measuring device 7, 8 and the display 10, as well as the conveying speed of the conveying device 12, can be known previously. In such a case, it is possible in accordance with the measured results of temperatures and electrification to identify plastics by marking them with given colored paints.

From the results shown in Table 1 and FIG. 2, one having a temperature after heating less than 40° C. can be marked with a red paint, for example. One having a temperature after heating equal to or more than 40° C. and a surface potential less than 1.5 kV can be marked with a blue paint as well. One having a temperature after heating equal to or more than 40° C. and a surface potential equal to or more than 1.5 kV can be marked with a yellow paint. Thus, it is possible to display PE with a red color, PMMA with a blue one and PVC with a yellow one. This method can retain forms of the plastics as such without crushing them and is accordingly effective in manual identification.

The thus-collected PE exhibits a high calorific value and can be used effectively as a raw material for a high-quality RDF. As for the collected PMMA, it can be reused alone or together with the collected PE after mixing at an adjusted mixing ratio as raw materials for blast furnaces or as materials for plastic products (hereinafter referred to as "material-recycle"). Furthermore, the collected PE and PMMA have high qualities of collections because PVC is not mixed in them. In addition, the collected PVC can be material-recycled as PVC.

Temperatures and surface potentials set for identifying plastics 11 have limitations that are optimally determined in accordance with the plastics 11 to be supplied. Types and colors of the paints applied for marking are suitably selected. The display 10 is equipped with a marking device, which marks the plastics 11 so that operators can perform identification work easily. The display 10 with the marking device that fits such a purpose can be applied to the plastic identifying apparatus of the present invention.

Far infrared rays commonly indicate electromagnetic waves that have wavelengths ranging between 5.6 μm and 1000 μm. As for far infrared heaters, those that can generate electromagnetic waves in the above range of wavelengths are applicable. Preferably, such far infrared heaters are efficiently that are designed to have the maximum radiation energy at wavelengths between 8 μm and 10 μm in particular, because this wavelength range increases differences between peaks of infrared absorption of the low exothermic plastic and PVC and peaks of infrared absorption of the high exothermic plastic. The far infrared heater may be provided with a concave reflector to collect far infrared rays efficiently. Among plastics of an identical material, those colored with a black color and transparent ones have a temperature difference equal to or less than 2° C. even though they are heated with far infrared rays under an identical condition. The temperature difference between a combination of the low exothermic plastic and PVC and the high exothermic plastic is equal to or more than 5° C. Therefore, the colored plastics give no problem in identification. On the other hand, electromagnetic waves having wavelengths less than 5.6 μm are called near-infrared rays. When a near-infrared heater that has larger radiation energy at these wavelengths is used, plastics can be heated more easily than when the far infrared heater is used. The near-infrared heater, however, gives a very small temperature difference between materials and melts black plastics and thin plastics. Thus, it cannot be applied to identification of materials. Preferably, the step of electrifying may be performed following the step of heating. When the object to be identified is a plastic waste, it may have water on its surface. The water on the surface is a factor that inhibits electrification. The step of heating can simultaneously perform drying to improve identification efficiency.

EXAMPLE 2

Figure 3:
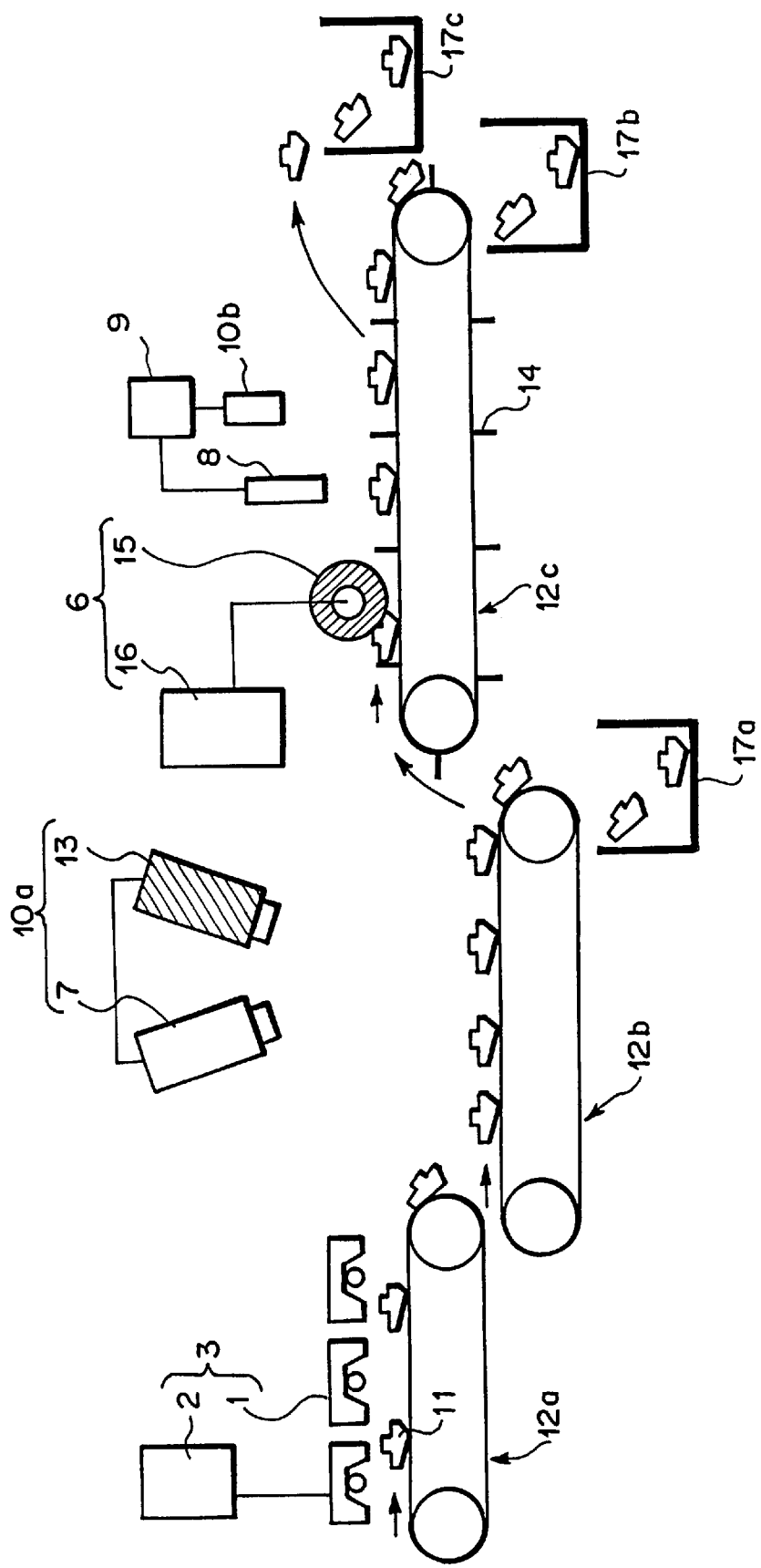
FIG. 3 is a schematic diagram showing another example of an apparatus for identifying plastics according to the present invention.

FIG. 3 is a schematic diagram showing another example of an apparatus for identifying plastics according to the present invention. A second example will be described using FIG. 3.

In Example 2, a heating device 3 is located above a conveying device 12a. Located above a conveying device 12b is a display 10a that includes a temperature-measuring device 7 and an image projection device 13. An electrifying device 6, an electrification-measuring device 8 and a display 10b are arranged in order above a conveying device 12c along the direction of supplying plastics 11. The conveying devices 12a, 12b, 12c of this example have metallic belt conveyers whose belt portions are grounded. The conveying devices 12c is provided with a stopper 14 that prevents the plastics 11 from moving beyond a given distance. The heating device 3 comprises a plurality of far infrared heaters 1 located above the conveying devices 12a and a temperature controller 2 that controls the heaters to apply constant far infrared rays on the plastics 11. The temperature-measuring device 7 uses an infrared thermograph to measure a two-dimensional distribution of temperatures and inputs measured image data into the image projection device 13. The image projection device 13 is set so that it can project the image data on the same region as a field measured by the temperature-measuring device 7. The image projection device 13 is capable of color-displaying only parts that have temperatures equal to or more than a given temperature. The electrifying device 6 includes a roller 15 and a rotation/pressure controller 16. The roller 15 has a surface coated with soft PVC that contains 30% by weight of a plasticizer. The surface of the roller 15 is used as a fixing portion to fix a frictional medium thereon. The roller 15 can press the plastics 11 with a force of 590 kPa (5 kgf/cm$^2$) or more. The rotation/pressure controller 16 can control the revolution number and pressure of the roller 15. In the electrification-measuring device 8, a plurality of surface potential sensors is arranged above the conveying device 12c to measure a two-dimensional distribution of surface potentials. The surface potential sensors use an electrostatic induction phenomenon, in which electric charges are generated on a metal that closes to the surface charges on the object, and monitor amounts of charges generated on small metallic plates to measure surface potentials on the objects. The two-dimensional measured results are input to the display 10b from the electrification-measuring device 8 through the controller 9. The display 10b determines an object that satisfies a preset surface potential to identify it as an identified object and marks it with a bit of paint.

For example, PE, polypropylene (hereinafter referred to as "PP"), PS, PET, PMMA and acrylonitrile-butadiene-styrene copolymer (hereinafter referred to as "ABS") are mixed in a mixture of plastics. This case is described below. These plastics are in the form of products such as bags and bottles.

PE and PP have components consisting only of carbon and hydrogen atoms and calorific values equal to or more than that of the petroleum. PE has a calorific value of 11,000 kcal/kg; PP, 10,500 kcal/kg; and the petroleum, about 10,300 kcal/kg. On the other hand, PS, PET, PMMA and ABS contain oxygen and nitrogen atoms and a benzene ring as components and accordingly have calorific values less than that of the petroleum (reference: Katsuhide MURATA, "System for producing powder fuels from refuse plastics", Chemical Device, Feb. 1995, p34, 1995).

Figure 4:
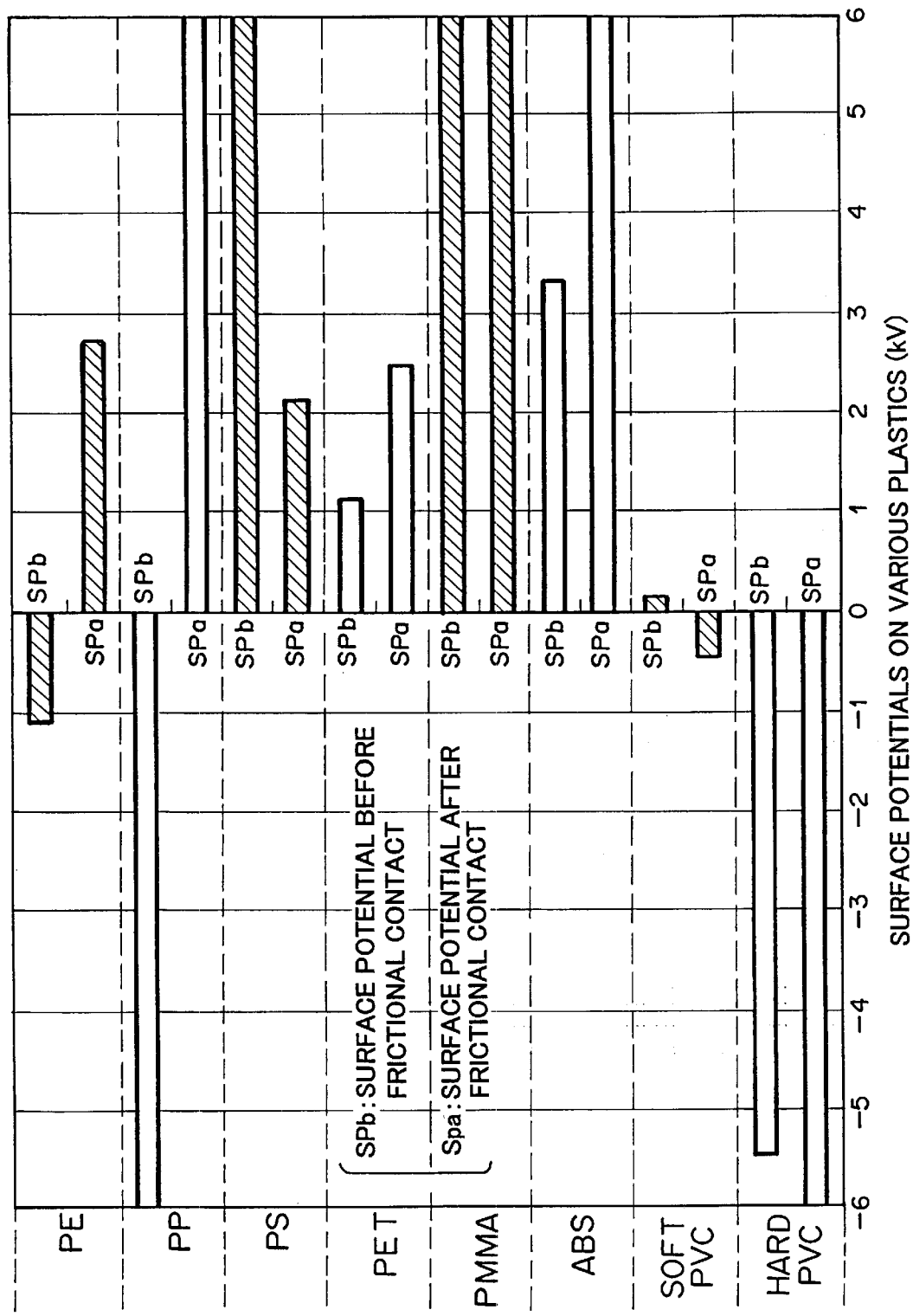
FIG. 4 shows surface potentials on frictionally electrified plastics.

FIG. 4 shows surface potentials on various plastics. Each test fragment of the plastics has a size of 50 mm×50 mm and is frictionally electrified 10 times each by contacting it on a piece of soft PVC under an applied force of 590 kPa (5 kgf/cm$^2$) with a moving distance of 100 mm.

From the results shown in Table 1 and FIG. 4, among temperature data measured by the temperature-measuring device 7, the image projection device 13 is assumed to project a red color only on those that have temperatures equal to or more than 40° C. In such a case, the temperature-measuring device 7 has the same field as that of the image projection device 13. Therefore, plastics with lower calorific values than that of the petroleum, for example, PS, PET, PMMA, ABS and PVC are displayed with a red color and are conveyed over the conveying device 12b. Accordingly, the operators can easily identify these plastics and transfer them to the next conveying device 12c. PE and PP, which are high exothermic plastics, are collected at a collecting section 17a. The low exothermic plastics and PVC, supplied to the conveying device 12c, are pressed under the roller 15 and frictionally contacted with the soft PVC on the surface of the roller 15, thereby allowing their surfaces being electrified.

The electrification-measuring device 8 measures surface potentials and sends them via the controller 9 to the display 10b, which can mark with a bit of red paint parts that have surface potentials of +1.0 kV or more, for example. In such a case, the operators can easily identify the low exothermic plastics such as PS, PET, PMMA and ABS, which are collected into a collecting section 17c. Remaining PVC is collected into a collecting section 17b.

The thus-collected PE and PP exhibits high calorific values and can be used effectively as raw materials for the high-quality RDF. As for the collected PS, PET, PMMA and ABS, they can be material-recycled alone or together with the collected PE and/or PP after mixing at an adjusted mixing ratio as raw materials for blast furnaces or as materials for plastic products. Furthermore, the collected high and low exothermic plastics have high qualities of collections because PVC is not mixed in them. In addition, the collected PVC can be material-recycled as PVC.

Assuming from an electrification row, PE and PP should be charged positively. It has been found from FIG. 4., however, that PE, PP and PVC may be charged to have opposite polarities depending on conditions because they have close positions on the electrification row. Therefore, it is difficult for the method using the frictional electrification to identify the high exothermic PE and PP from PVC. On the other hand, it is possible to identify the high exothermic PE and PP from PVC according to the present invention. That is, the use of far infrared heating together with electrification for the first time leads to classifying of waste plastics into three groups consisting of high exothermic plastics, low exothermic plastics and PVC while remaining their product forms efficiently.

The electrifying device 6 may comprise a mechanism that can contact the frictional medium efficiently with the plastics 11 to be identified. For instance, such a mechanism can be applied that moves up or down a rotary brush having a brush of soft PVC as the frictional medium or a plurality of rods having surfaces coated with soft PVC to strike and frictionally electrify the plastics. Furthermore, rollers, rotary brushes and striking rods can be used together.

Previous corona electrification to electrify all plastics 11 positively, followed by frictional electrification as shown in example 1 enlarges a difference between the surface potential of PVC and those of other plastics and improves the identification ratio.

Temperatures and surface potentials set for identifying plastics 11 have limitations that may be optimally determined in accordance with the plastics 11 to be supplied. Types and colors of the paints applied for marking may also be suitably selected. The display 10b is equipped with a marking device, which marks the plastics 11 so that operators can perform identification work easily. The display 10b with the marking device that fits such a purpose can be applied to the plastic identifying apparatus of the present invention.

EXAMPLE 3

Figure 5:
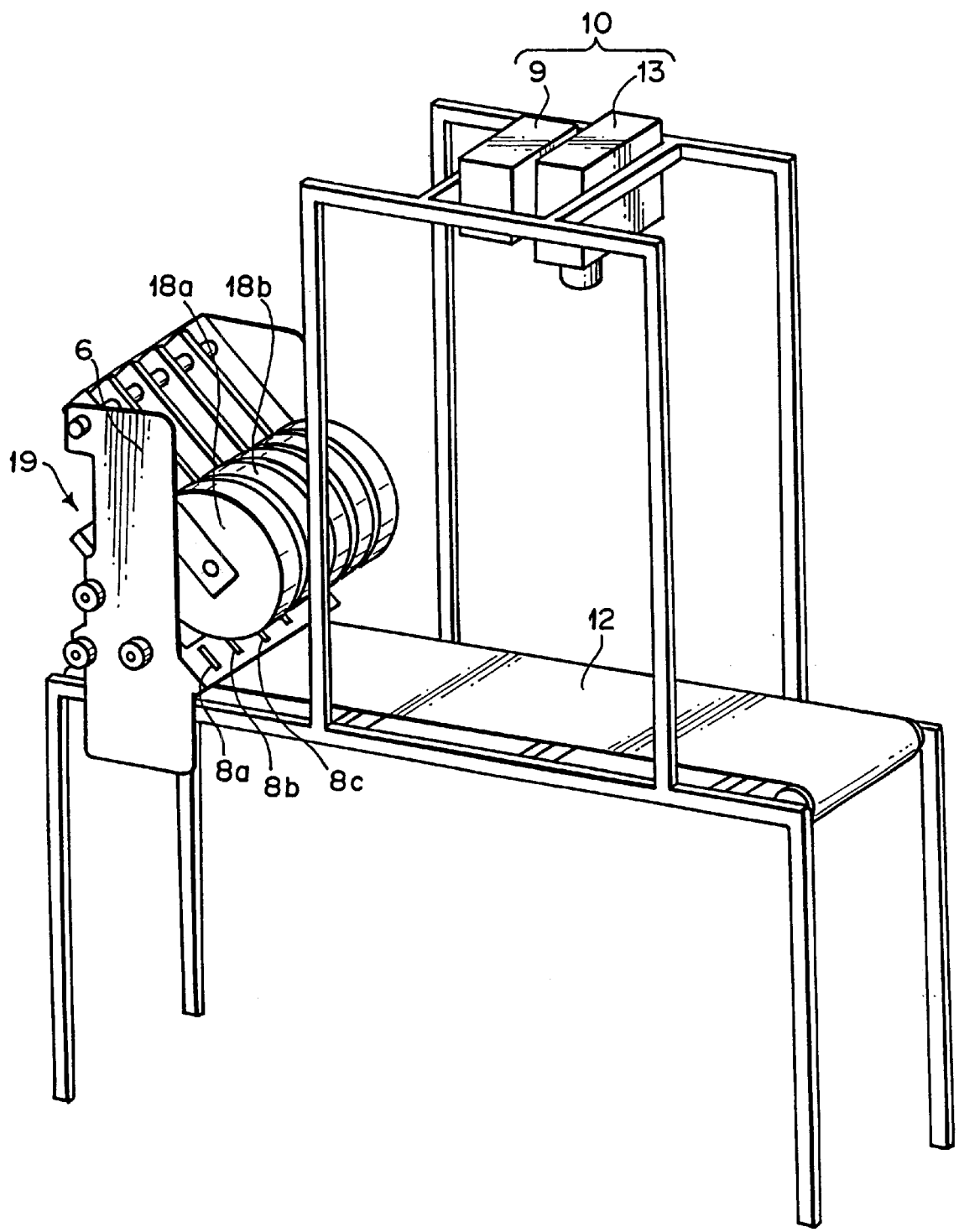
FIG. 5 is a schematic diagram showing an example of an electrifying device, an electrification-measuring device and a display in the apparatus for identifying plastics according to the present invention.
Figure 6:
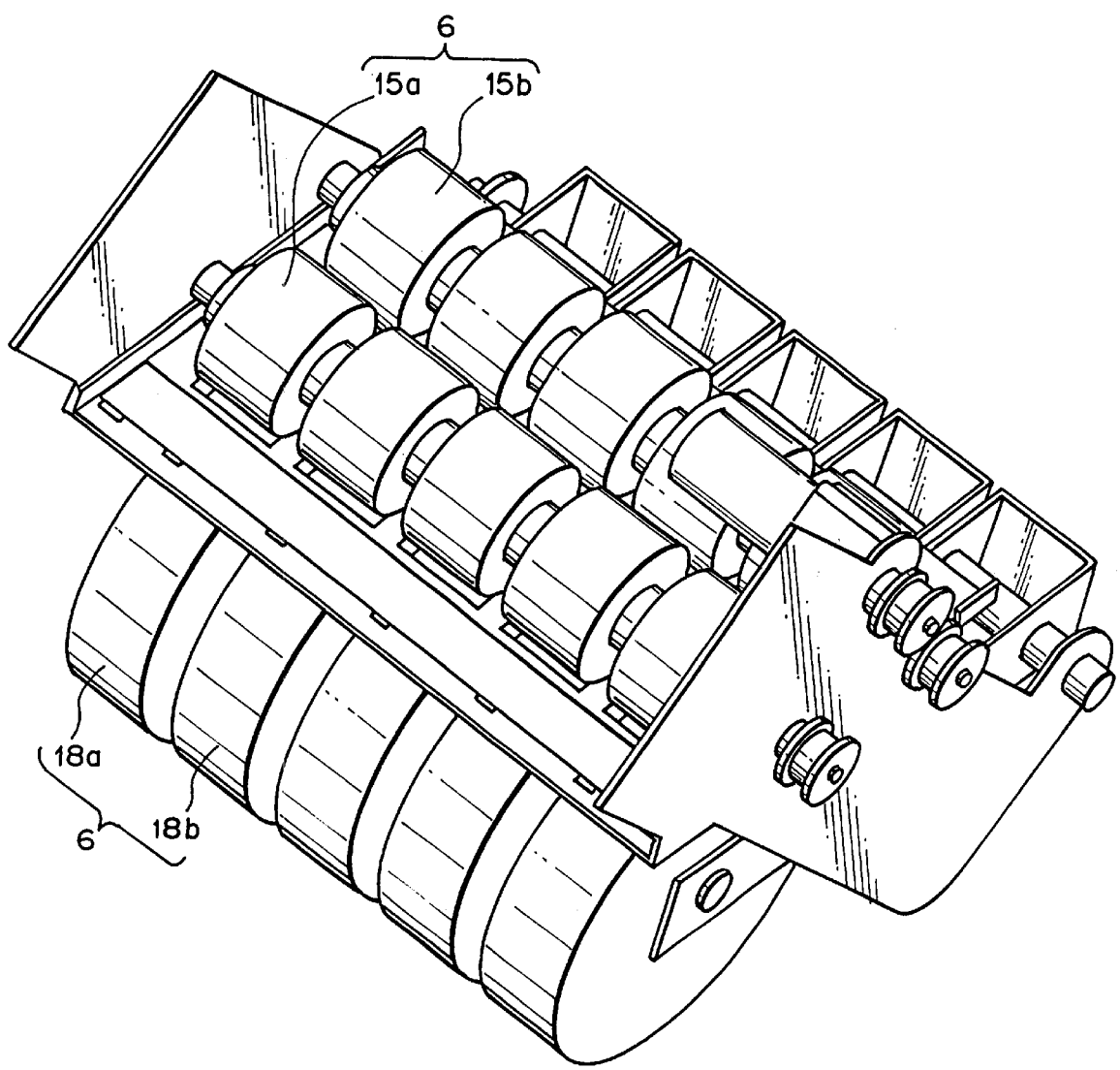
FIG. 6 is a schematic diagram showing an example of an electrifying device in the apparatus for identifying plastics according to the present invention.

FIG. 5 is a schematic diagram showing another example of an electrifying device 6, an electrification-measuring device 8 and a display 10 in an apparatus for identifying plastics according to the present invention. FIG. 6 is a schematic diagram showing the electrifying device in FIG. 5 upside down. A third example will be described using FIGS. 5 and 6.

Plastics are supplied in the electrifying device 6 along a supplying direction 19 through rollers 15 and auxiliary rollers 18 located above and opposite to the rollers 15. The plastics are frictionally electrified with frictional media secured on surfaces of the rollers 15, used as fixing sections, in FIG. 6. In this case, adjustment of pressures applied on the plastics from the auxiliary rollers 18 can control amounts of electrification. Although the plastics have charged regions at lower surfaces, the state of electrification can be measured if the rollers 15 are located in the proximity of the electrification-measuring device 8 as shown in FIG. 5. The electrification-measuring device 8 of FIG. 5 has a structure in which a plurality of surface electrometers is arranged laterally. Outputs from the surface electrometers are converted into image signals at a signal processor not depicted and are input into a controller 9 in a display 10 to control an image projection device 13. For example, on the basis of the electrostatic results from FIG. 4, when a surface potential of +1.0 kV or more is obtained, a specific signal is input from the signal processor to the controller 9. When the signal processor monitors the conveying speed of the conveying device 12, it is easy to determine a position on the conveying device 12 where a part with a surface potential of +1.0 kV or more is located after measurement of surface potentials. Successive measured results of surface potentials and the corresponding positions of plastics are converted into two-dimensional image data and only the part with +1.0 kV or more is displayed with a red color. The image projection device 13 may project this image so that the projection field is superimposed on the real to mark the object to be identified. If PVC and the low exothermic plastics such as PS, PET, PMMA and ABS are fed into the electrifying device 6 under this condition, PET, PMMA and ABS are marked with a red color to identify them from PVC. The identification efficiency improves if the number of the electrification-measuring devices 8 increases and an interval for arranging them reduces.

EXAMPLE 4

Figure 7:
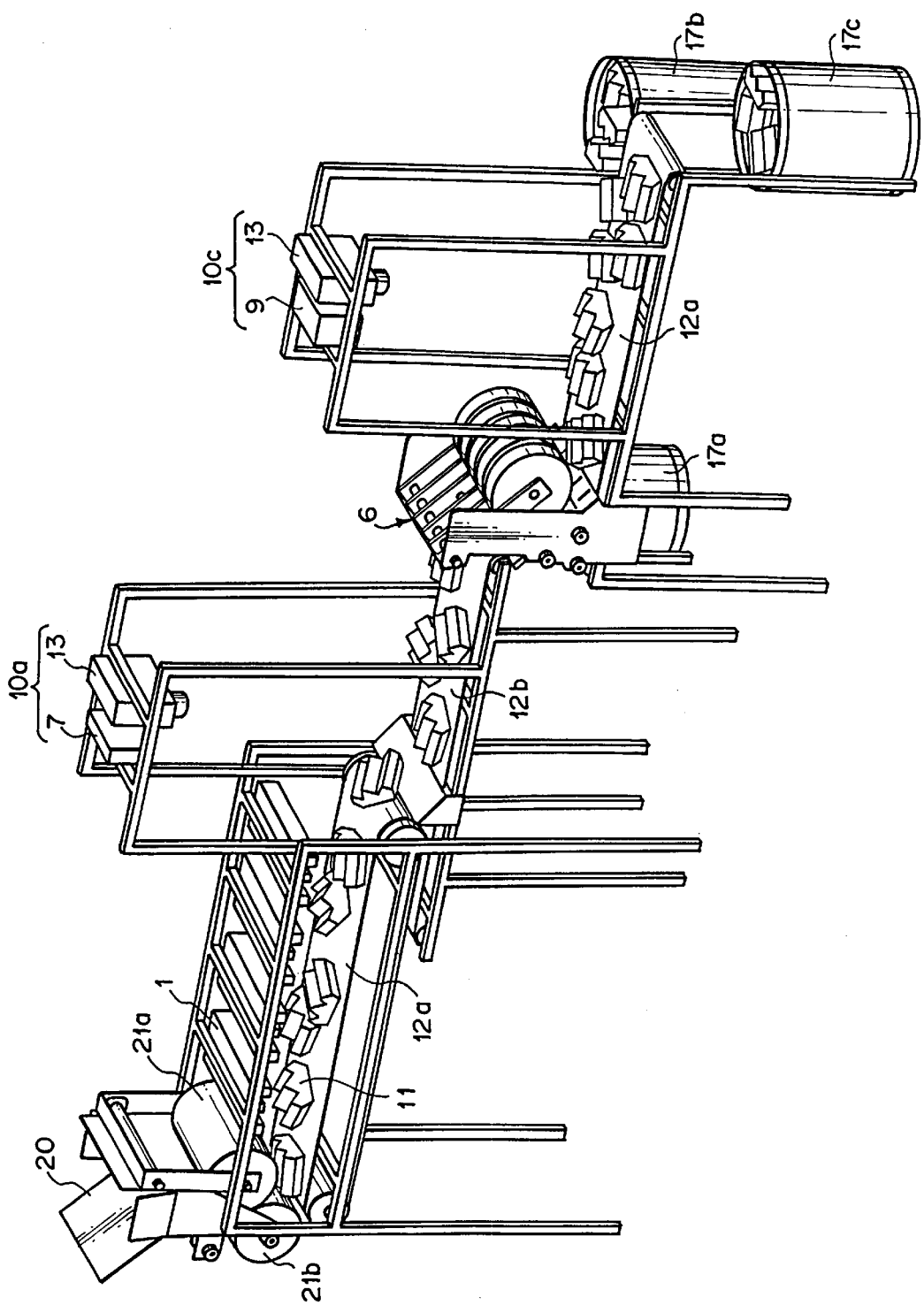
FIG. 7 is a schematic diagram showing a further example of an apparatus for identifying plastics according to the present invention.

FIG. 7 is a schematic diagram showing a further example of an apparatus for identifying plastics according to the present invention. A fourth example will be described using FIG. 7.

FIG. 7 shows an arrangement, in which, following the heating device 3 and the display 10a of the second example, the electrifying device 6 and the display 10c of the third example are located. Plastics, fed into a supply hopper 20, are compressed at compressive rollers 21a and 21b and then identified through the process steps of heating, identifying, electrifying and identifying. For example, when a mixture of high exothermic plastics, low exothermic plastics and PVC is fed into the supply hopper 20, those heated up to or above a given temperature are marked with a given color as the low exothermic plastic and PVC. On the other hand, the high exothermic plastics are not marked. In the system arrangement of this example, the high exothermic plastics that are not marked are removed manually. The remaining low exothermic plastic and PVC are sent to the step of electrification, and those charged up to or above a given surface potential are marked with a given color as the low exothermic plastic and removed manually. The remainders in this case are collected as PVC. It can be suitably selected to remove those that are marked or those that are not marked in accordance with the types and amounts of objects to be identified, the identification efficiency and the system arrangement. In addition, values of temperature and surface potential to identify can be suitably determined in response to types of plastics to be supplied and purposes of collection. For example, when it is desired to identify only hard PVC, a part with a surface potential equal to or below −1.0 kV may be marked with a red color on the basis of the results in FIG. 4.

Depending on three-dimensional forms of the plastics, a part to which far infrared rays cannot be applied effectively possibly remains as well as a shade when a ray of light is illuminated. On the other hand, areas radiated with far infrared rays increase and the identification efficiency improves if the plastics are compressed prior to application of far infrared rays.

According to the method and apparatus for identifying plastics of the present invention, unknown plastics can be identified efficiently. In particular, high exothermic PE and PP, low high exothermic PS, PET, PMMA and ABS, and PVC can be efficiently identified among wastes that hold forms of products as such without crushing them. Therefore, an appropriate processing and recycling of wastes can be achieved.

Having described the embodiments consistent with the present invention, other embodiments and variations consistent with the present invention will be apparent to those skilled in the art. Therefore, the invention should not be viewed as limited to the disclosed embodiments but rather should be viewed as limited only by the spirit and scope of the appended claims.

What is claimed is:

1. A method of identifying plastics comprising:
   heating and electrifying a mixture of at least two plastics; and
   measuring heating properties and electrostatic properties thereof to identify said plastics.

2. The method of identifying plastics as recited in claim 1, wherein said mixture includes at least one low exothermic plastic, at least one high exothermic plastic, and polyvinyl chloride.

3. The method of identifying plastics as recited in claim 2, wherein said low exothermic plastic has, as essential components, polystyrene, polyethylene terephthalate, acrylonitrile-butadiene-styrene copolymer and methacrylic resin.

4. The method of identifying plastics as recited in claim 2, wherein said high exothermic plastic has, as essential components, polyethylene and polypropylene.

5. The method of identifying plastics as recited in claim 1, wherein said heating comprises radiation of far infrared rays.

6. The method of identifying plastics as recited in claim 1, wherein said electrifying comprises any one of corona discharge, frictional electrification, and a combination of corona discharge and frictional electrification.

7. The method of identifying plastics as recited in claim 1, wherein said mixture comprises plastic products or wastes of plastic products.

8. The method of identifying plastics as recited in claim 7, wherein said mixture is not crashed.

9. A method of identifying plastics comprising:
   heating, followed by electrifying, a mixture of at least two plastics; and
   measuring heating properties and electrostatic properties thereof to identify said plastics.

10. The method of identifying plastics as recited in claim 9, wherein said mixture includes at least one low exothermic plastic, at least one high exothermic plastic, and polyvinyl chloride.

11. The method of identifying plastics as recited in claim 10, wherein said method comprises heating said mixture to identify said high exothermic plastic on the basis of a difference in heating property, followed by electrifying a mixture of said low exothermic plastic and said polyvinyl chloride to identify said polyvinyl chloride on the basis of a difference in electrostatic property.

12. The method of identifying plastics as recited in claim 10, wherein said low exothermic plastic has, as essential components, polystyrene, polyethylene terephthalate, acrylonitrile-butadiene-styrene copolymer and methacrylic resin.

13. The method of identifying plastics as recited in claim 10, wherein said high exothermic plastic has, as essential components, polyethylene and polypropylene.

14. The method of identifying plastics as recited in claim 9, wherein said heating comprises radiation of far infrared rays.

15. The method of identifying plastics as recited in claim 9, wherein said electrifying comprises any one of corona discharge, frictional electrification, and a combination of corona discharge and frictional electrification.

16. The method of identifying plastics as recited in claim 9, wherein said mixture comprises plastic products or wastes of plastic products.

17. The method of identifying plastics as recited in claim 16, wherein said mixture is not crushed.

18. An apparatus for identifying plastics comprising:
a heating device for heating said plastics;
an electrifying device for electrifying said plastics;
a temperature-measuring device for measuring temperatures of said plastics;
an electrification-measuring device for measuring charged states of said plastics;
a display for displaying measured results of said temperatures; and
a display for displaying measured results of said charged states, wherein said apparatus is operable in accordance with said method of identifying plastics as recited in any one of claims 1–9.

19. The apparatus for identifying plastics as recited in claim 18, wherein said heating device comprises a device that uses far infrared rays.

20. The apparatus for identifying plastics as recited in claim 19, wherein said heating device comprises a far infrared heater and a concave reflector, said reflector collecting far infrared rays to apply them on an object to be heated.

21. The apparatus for identifying plastics as recited in claim 18, wherein said electrifying device comprises a device that is operable in away according to any one of corona discharge, frictional electrification, and a combination of corona discharge and frictional electrification.

22. The apparatus for identifying plastics as recited in claim 21, wherein said electrifying device comprises a plurality of stylus-like protrusions; corona discharge electrodes configured with fixed portions of said protrusions; and a power supply for applying a DC or AC voltage on said corona discharge electrodes.

23. The apparatus for identifying plastics as recited in claim 21, wherein said electrifying device comprises a frictional medium; a fixing section for fixing said frictional medium; and a containing section for containing said frictional medium.

24. The apparatus for identifying plastics as recited in claim 23, wherein said frictional medium is one selected from the group consisting of a roller, a blush and a rod.

25. The apparatus for identifying plastics as recited in claim 23, wherein said electrifying device comprises a roller-like frictional medium and an auxiliary roller opposite thereto, said electrifying device interposing said plastics between said frictional medium and said auxiliary roller to frictionally electrifying said plastics.

26. The apparatus for identifying plastics as recited in claim 23, where in said frictional medium has a portion composed of polyvinyl chloride for coming in contact with said plastics.

27. The apparatus for identifying plastics as recited in claim 26, wherein said polyvinyl chloride comprises soft polyvinyl chloride alone or a mixture of soft polyvinyl chloride and a plasticizer of 25–50% by weight of said mixture.

28. The apparatus for identifying plastics as recited in claim 18, wherein said temperature-measuring device comprises a device for outputting said measured results of said temperatures to said display as temperature image data.

29. The apparatus for identifying plastics as recited in claim 28, wherein said display comprises a device for image-projecting said temperature image data input as such on said object measured by said temperature-measuring device.

30. The apparatus for identifying plastics as recited in claim 28, wherein said display comprises a marking means for adding identified marks on said plastics, said marks being classified on the basis of measured data input.

31. The apparatus for identifying plastics as recited in claim 18, wherein said electrification-measuring device comprises a device for measuring surface charges, surface potentials, or surface charges together with surface potentials on said plastics and outputting them to said display as charged data.

32. The apparatus for identifying plastics as recited in claim 31, wherein said display comprises a device for image-projecting said charged data input as such on said object measured by said electrification-measuring device.

33. The apparatus for identifying plastics as recited in claim 31, wherein said display comprises a marking means for adding identified marks on said plastics, said marks being classified on the basis of measured data input.

* * * * *